United States Patent [19]

Fong

[11] 4,384,975

[45] May 24, 1983

[54] PROCESS FOR PREPARATION OF MICROSPHERES

[75] Inventor: Jones W. Fong, Parsippany, N.J.

[73] Assignee: Sandoz, Inc., East Hanover, N.J.

[21] Appl. No.: 159,148

[22] Filed: Jun. 13, 1980

[51] Int. Cl.$^3$ ............ B01J 13/02; A01N 25/28; A61K 9/26; A61K 9/52

[52] U.S. Cl. .................. 427/213.36; 71/64.11; 71/DIG. 1; 424/19; 424/22; 424/33; 424/35; 427/213.3

[58] Field of Search ............. 252/316; 424/33, 35, 424/19, 22

[56] References Cited

U.S. PATENT DOCUMENTS

| | | | |
|---|---|---|---|
| 3,429,827 | 2/1969 | Ruus | 252/316 |
| 3,575,882 | 4/1971 | Vandegaer et al. | 252/316 |
| 3,577,515 | 5/1971 | Vandegaer | 424/32 |
| 3,872,023 | 3/1975 | Baum et al. | 252/316 |
| 3,960,757 | 6/1976 | Morishita et al. | 252/316 |
| 4,166,800 | 9/1979 | Fong | 252/316 |

FOREIGN PATENT DOCUMENTS

| | | | |
|---|---|---|---|
| 1188957 | 4/1970 | United Kingdom | 424/37 |
| 1371179 | 10/1974 | United Kingdom | 424/32 |
| 1543454 | 4/1979 | United Kingdom | 252/316 |

*Primary Examiner*—Richard D. Lovering
*Attorney, Agent, or Firm*—Gerald D. Sharkin; Robert S. Honor; Walter F. Jewell

[57] ABSTRACT

Microspheres, prepared by solvent removal from an oil-in-water emulsion using carboxylic acid salt surfactant, e.g., sodium oleate as the emulsifier.

16 Claims, No Drawings

PROCESS FOR PREPARATION OF MICROSPHERES

BACKGROUND OF THE INVENTION

This invention relates to microspheres. More particularly it relates to processes for the preparation of microspheres of a polymer and a core material and to products produced thereby. In one particular aspect it relates to processes for the preparation of microspheres of a polymer and a drug and to products produced thereby.

Broadly, the microspheres of this invention may be described as: microcapsules of a core material, e.g., drug, and a polymer wherein the polymer coats a drug particle; or microprills which are homogeneous mixtures of a core material, e.g., drug and a polymer. The processes of this invention are directed to the preparation of microspheres by the novel use of carboxylic acid salt surfactants as emulsifiers in oil-in-water emulsions which utilize solvent removal techniques to isolate the discrete microspheres.

Microencapsulation processes based on solvent removal from emulsions are known in the prior art and have been reviewed in various publications. These include: M. Morishita et al in "Microencapsulation: Processes and Applications," edited by J. E. Vandegaer, Plenum Press, NY, 1974, pp. 115-116; A. Watanabe and T. Hayashi in "Microencapsulation," edited by J. R. Nixon, Marcel Dekker, Inc., NY, 1976, pp. 18-19; A. Kondo, "Microcapsule Processing and Technology," edited and revised by J. W. Van Valkenburg from the original 1970 Japanese edition, Marcel Dekker, Inc., NY, 1979, pp. 106-120.

The basis of the prior art processes involves dissolving or dispersing the core material in a solution of the wall-forming material dissolved in a volatile, water-immiscible organic solvent. The organic phase is emulsified with an aqueous solution containing a surface active agent to form a dispersion of oil droplets which would yield microspheres upon removal of the organic solvent by evaporation (distillation or spray-drying), solvent extraction or freeze-drying. However, the products from these processes are agglomerated microspheres and not discrete particles, suitable for example, in parenteral applications.

Solvent removal from an emulsion is disclosed in U.S. Pat. Nos. 3,523,906 and 3,523,907 wherein an aqueous solution was encapsulated as core material by the emulsion method using a hydrophilic colloid such as gelatin or polyvinyl alcohol as the emulsifier.

The use of the emulsion process for microencapsulation of medicaments is described in U.S. Pat. No. 3,960,757 wherein a hydrophilic colloid (e.g., gelatin, polyvinyl alcohol) and/or a surface active agent (anionic or nonionic type having an HLB of not less than 10) is used as the emulsifier.

A mixed gelatin-nonionic surface active agent system in a similar process for preparing beads of biodegradable polymer e.g., polylactic acid containing progesterone was used by S. Yolles et al in "Controlled Release Polymeric Formulations," edited by D. R. Paul and F. W. Harris, American Chemical Society, Washington, D.C., 1976, pp. 124-125. The microspheres formed were 250-420 micron diameter with some agglomerates present.

An anionic surfactant, sodium dodecyl sulfate, utilizing the emulsion process to encapsulate pesticides with polylactic acid is described by H. Jaffe in U.S. Pat. No. 4,272,398. The product was a coarse powder of large aggregates of microspheres, most of which were 177-595 microns.

U.S. Pat. No. 3,660,304 discloses a method for producing oily liquid-containing microcapsules using a mixture of high and low boiling point solvents, in an oil-in-water emulsion system. There is no distinction or appreciation of the differences in performance between the many classes of surface active agents in the encapsulation process. Fatty acid salts are mentioned among the many surface active agents disclosed.

Polyvinyl alcohol was employed as the emulsifier in a solvent evaporation process for obtaining microspheres of polylactic acid by L. R. Beck et al, "A New Long-Acting Injectable Microcapsule System for the Administration of Progesterone," Fertility and Sterility 31:5, 545-551 (1979). The microspheres were 10-250 microns and were free of agglomerates.

Using biodegradable polymers such as polylactic acid as the wall-forming material in microspheres for injectable application eliminates the need for surgical removal of the microspheres after delivery of the drug. For controlled release of drug suitable for parenteral administration, the microspheres should be free of agglomerates and the size should be large enough to provide adequate duration of release yet small enough not to restrict passage through the standard syringe needles. Thus, the maximum size would be about 150 microns for a conventional No. 20 gauge needle. Except when polyvinyl alcohol was employed as the emulsifier, agglomerates were reported to be present, and the 150 micron size limitation was greatly exceeded in the above prior art references preparing microspheres with polylactic acid.

However, polyvinyl alcohol is listed in the 1976 Registry of Toxic Effects of Chemical Substances. It has been implicated as being carcinogenic when introduced parenterally into animals, according to W. C. Hueper, "Carcinogenic Studies on Water-Soluble and Insoluble Macromolecules," Archives of Pathology, 67, 589-617 (1959). Residual amounts of occluded polyvinyl alcohol in the microspheres due to the interfacial property of emulsifier would be undesirable for injectable pharmaceutical application.

Thus, there is no satisfactory emulsifier reported in the prior art for microencapsulation processes based on solvent removal from aqueous emulsions, which produce discrete, non-agglomerated microspheres suitable both for pharmaceutical and non-pharmaceutical applications.

SUMMARY OF THE INVENTION

Broadly, this invention provides for the production of microspheres in an oil-in-water emulsion process using a carboxylic acid salt surfactant, e.g., sodium oleate as an emulsifier, whereby solvent removal from the oil phase allows for isolation of discrete microspheres.

The microcapsules of this invention comprising a polymer and a core material, e.g, drug, may be prepared by dissolving the polymer in a volatile, water-immiscible organic solvent in which the drug is not soluble; adding the drug particles; mixing the organic dispersion with an aqueous solution containing a carboxylic acid salt as the emulsifer to form a stable oil-in-water emulsion; and removing the organic solvent by evaporation to form discrete microcapsules.

The microprills of this invention comprising a homogeneous mixture of polymer and core material, e.g., drug, may be prepared by dissolving both the polymer and drug in a volatile, water-immiscible organic solvent; mixing the organic phase with an aqueous solution containing a carboxylic acid salt as the emulsifier to form a stable oil-in-water emulsion; and removing the organic solvent by evaporation to form discrete microprills.

The essential feature of this invention is the use of a carboxylic acid salt surfactant as the emulsifier to stabilize the oil-in-water emulsion against uncontrolled agglomeration and coalescence during solvent removal, allowing isolation of discrete microspheres.

DESCRIPTION OF THE PREFERRED EMBODIMENT

The formation of microcapsules of this invention is based on solvent removal from an oil-in-water emulsion. When an emulsion containing oil droplets formed from a dispersion of solid drug particles in a polymer solution is being evaporated, the initial removal of solvent causes the polymer to precipitate in a viscous liquid state and envelope the solid drug particles while maintaining the spherical configuration. Complete removal of solvent yields hardened, hetereogeneous microcapsules of polymer and drug particles.

The formation of microprills of this invention is also based on solvent removal from an oil-in-water emulsion. When an emulsion containing oil droplets formed from a homogeneous solution of polymer and drug is being evaporated, the initial removal of solvent causes both the polymer and drug to precipitate together in a viscous, liquid state while maintaining the spherical configuration. Complete removal of solvent yields hardened, homogeneous microprills of polymer and drug.

The most critical aspect of these processes involves using an effective emulsifier. The surfactant used as the emulsifier must first stabilize the oil-in-water emulsion containing the polymer-drug-solvent system against coalescing into larger droplets and subsequent "breaking" of the emulsion. As the solvent is being evaporated, the emulsifier must also maintain these oil droplets in their spherical configuration and stabilize them against uncontrolled agglomeration until solvent removal is completed so that the hardened microspheres can be isolated as discrete particles.

The encapsulation processes disclosed in U.S. Pat. No. 3,960,757 above teaches the use of a surface active agent having a Hydrophile-Lipophile Balance (HLB) value of not less than 10.

The following emulsifying agents with high HLB values (for oil-in-water emulsion) were evaluated for their effectiveness in microencapsulation processes following the teaching of this invention;

| Manufacturer | | Generic Name | HLB |
|---|---|---|---|
| Atlas | BRIJ | 58 Polyoxyethylene Cetyl Ether | 15.7 |
| | | 78 Polyoxyethylene Stearyl Ether | 15.3 |
| | | 98 Polyoxyethylene Oleyl Ether | 15.3 |
| BASF | Chremophor EL | Glycerol Polyethylene Glycol Oxystearate | 13 |
| | RH | 40 Glycerol Polyethylene Glycol Oxystearate | 15 |
| | RH | 60 Glycerol Polyethylene Glycol Oxystearate | 16 |
| Atlas | MYRJ | 45 Polyoxyethylene Stearate | 11.1 |
| | | 52 " | 16.9 |

-continued

| Manufacturer | | Generic Name | HLB |
|---|---|---|---|
| | | 53 " | 17.9 |
| Atlas | Tween | 20 Polyoxyethylene Sorbitan Monolaurate | 16.7 |
| | | 21 Polyoxyethylene Sorbitan Monolaurate | 13.3 |
| | | 40 Polyoxyethylene Sorbitan Monopalmitate | 15.6 |
| | | 60 Polyoxyethylene Sorbitan Monostearate | 14.9 |
| | | 80 Polyoxyethylene Sorbitan Monooleate | 15.0 |

Each of the above emulsifying agents were evaluated for their effectiveness in forming a stable emulsion between methylene chloride and water. None of the above emulsifying agents provided a sufficiently stable emulsion.

The HLB method is only useful as a general guide to selection of surface active agents, based on the type of emulsion desired. For example, materials with high HLB values (8 to 18) are oil-in-water emulsifiers and those with low HLB values (3 to 6) are water-in-oil type. However, the HLB method does not indicate the efficiency (required concentration) nor the effectiveness (stability of the emulsion) of the surfactant. Therefore selecting an appropriate emulsifier requires more than just a consideration of HLB values. The subject of HLB method was reviewed by M. J. Rosen, "Surfactants and Interfacial Phenomena," John Wiley & Sons, Inc., 1978, pp. 242–245.

In contrast to the teaching of U.S. Pat. No. 3,960,757, a surface active agent having an HLB value of not less than 10 is not a reliable indicator of an effective emulsifier in the microencapsulation processes of this invention. Furthermore, unsatisfactory results were also obtained when the hydrophilic colloids of U.S. Pat. No. 3,960,757 were used for the preparation of microspheres. Using gelatin as the hydrophilic colloid resulted in a coarse powder of small agglomerates, whereas acacia gum as the hydrophilic colloid resulted in massive agglomeration.

This invention is based on the unexpected discovery that discrete microspheres of a polymer and a core material can be obtained using a carboxylic acid salt surfactant as the emulsifying agent.

Examples of carboxylic acids whose salts are useful according to this invention include straight-chain fatty acids, coconut fatty acids, conjugated sarcosine, or N-acylated bile acids, e.g., glycocholic acid and chlolic acid, and the like. The salts can be the alkali metal salts of the acid such as sodium and potassium salts or volatile amine salts of ammonia and triethanolamine. The emulsifiers can be used as the ready-made salts or generated in situ by adding carboxylic acid to the oil phase and alkaline material to the aqueous phase.

Salts of fatty acids, such as sodium oleate and potassium oleate, are especially preferred for preparing injectable microspheres of biodegradable polymers because the fatty acids, being endogenous lipids, are also biodegradable and nontoxic. Mixtures of fatty acid salts are within the scope of this invention. Also mixtures of the fatty acid salts with nonionic surface active agents or with hydrophilic colloids, e.g. gelatin, are within the scope of this invention. The concentration of the emulsifier in the present processes is not critical, provided it is above the critical micelle concentration of the emulsifier.

The fatty acid salt emulsifier of this invention used for the preparation of microspheres of biodegradable polymers, e.g., polylactic acid and drug, satisfy the three major prerequisites required for parenteral application:
(1) discrete microspheres, free of agglomerates, with maximum diameter of 150 microns,
(2) a release rate which is significantly slower than the non-encapsulated drug, and
(3) all ingredients in the microspheres, (even residual amounts), are non-toxic and pharmaceutically acceptable.

Furthermore, the microspheres of polylactic acid and drug made with a fatty acid salt as emulsifier have release rates which are superior to those made with gelatin. The release rates of microspheres made with gelatin as emulsifier are only slightly slower than the non-encapsulated drug. In addition, the gelatin product was a coarse powder of small agglomerates, not suitable for injectable application. The following is a comparison of the release rates of microspheres made with sodium oleate, and gelatin, together with non-encapsulated drug.

| Emulsifier | Size | % Drug Release (Bromocriptine) | | |
|---|---|---|---|---|
| | | 1 hr | 4 hr | 1 day |
| Microspheres Sodium Oleate[1] | 25-90 microns | 14 | 19 | 30 |
| Microspheres Gelatin[2] | coarse powder | 22 | 29 | 62 |
| Non-encapsulated Drug[3] | | 31 | 56 | 79 |

[1]Example 1
[2]Example 2
[3]bromocriptine mesylate

Since the emulsifiers of this invention are carboxylic acid salts, the aqueous phase may require a somewhat alkaline pH to prevent liberation of the free carboxylic acid. If the drug is in the form of its acid salt and an alkaline pH is required, this can be satisfied by the addition of alkali or an alkaline buffer solution. The alkaline pH may convert the drug to its free base form prior to encapsulation.

The emulsion processes require the drug to be insoluble or only slightly soluble in water. For drugs with some solubility in water, the aqueous phase can be saturated with the drug to maintain the desired concentration in the oil phase. An alternative is to add an inorganic salt to the aqueous solution to decrease solubility of the drug in the aqueous phase by the salting-out effect, provided the amount of electrolyte used does not adversely affect the performance of the emulsifier.

Natural and synthetic polymers may be used in the emulsion-based processes of this invention for the preparation of microspheres. However, the coating polymer must be soluble in a water-immiscible solvent. For example, the polymers include cellulosic polymers, polyvinyl acetate, polyvinyl chloride, natural and synthetic rubbers, polyacrylates, polystyrene and the like. When the microspheres of this invention are intended for injectable pharmaceutical applications, biodegradable polymers such as polylactic acid, polyglycolic acid, polyhydroxybutyric acid, polycaprolactone, polyalkylene oxalate, polyalkylene glycol esters of acids of the Kreb's e.g., citric acid cycle and the like and copolymers thereof may be utilized.

Illustrative of the Kreb's cycle di- and tri-carboxylic acids are citric, cis-aconitic, isocitric, α-ketoglutaric, succinic, fumaric, malic and oxaloacetic. These acids or their physiologically tolerable homologues are reacted with a biologically compatible polyol compound e.g., glycerol, or a compound based on such a polyol, e.g., an ester of glycerol, as set forth in U.S. Pat. No. 3,978,203. Among the physiologically tolerable polyols are glycerol, mannitol, sorbitol, and the like.

It is not necessary to be limited to a single polymer system and there may be advantages in using a mixture of polymers. For example, release rate characteristics may be altered by mixture of polymers differing in monomer composition, molecular weight, crystallinity, biodegradation rate and the like.

For the preparation of microprills, the solvent selected must dissolve both polymer and active agent. For the preparation of microcapsules, the solvent must dissolve the polymer but not the dispersed core materials, e.g., drug particles. For either microprills or microcapsules, the organic solvent used for the oil phase must be immiscible or only partly soluble in water, relatively volatile, and inert to both polymer and drug.

Examples of the water-immiscible solvent for the biodegradable polylactic acid polymer and its copolymers include methylene chloride, chloroform, benzene, ethyl acetate and the like.

The solvent need not be limited to a single component system and mixed solvent systems may be used. Where there is no common solvent for both the polymer and core material a mixed system may act as a common solvent in preparing microprills. For example, it may be necessary to predissolve the drug in a small volume of a water-miscible solvent before mixing with the water-immiscible solution. A variation of this mixed solvent system for the preparation of microcapsules is where the core material particles to be encapsulated have some solubility in the solvent of choice for the polymer. Sufficient amount of another solvent may then be added to minimize drug solubility without affecting polymer solubility.

For the preparation of heterogeneous microcapsules in which the drug is insoluble or partially soluble in the organic solvent of choice, the drug particle size should be reduced for efficient microencapsulation. This can be done by micronization of the drug substance prior to dispersing in the oil phase or by mixing the drug particles-organic dispersion with an ultrasonic homogenizer prior to the emulsification step.

Solvent removal by evaporation after the emulsification step can be controlled by temperature with or without reduced pressure. This can be conducted by distillation at ambient temperature or at lower or elevated temperatures. It may also be advantageous to employ a sequential change in temperature and pressure. Solvent removal can also be accomplished by spray-drying, solvent extraction or freeze-drying the emulsion.

The core material of the microspheres prepared by the processes of this invention may be agricultural agents such as insecticides, fungicides, herbicides, rodenticides, pesticides, fertilizers, and viruses for crop protection and the like; cosmetic agents such as deodorants, fragrances and the like; food additives such as flavors, oils, fats and the like; and pharmaceutical agents.

Pharmaceutical agents, e.g., drugs, are especially preferred core materials and the invention will be further described using drugs as the core material. These drugs may be in free base form or in the form of their nontoxic, pharmaceutically acceptable acid addition salts, although the latter may be converted to the free base form by the alkaline pH used in these emulsion processes. Representatives of such salts are hydrochloride, sulfate, phosphate, succinate, benzoate, acetate, pamoate, fumarate, mesylate and the like.

The polymer-drug compositions may also include controlled release injectable, oral and topical formulations. Other pharmaceutical applications may include taste-masking of bitter drugs, separation of incompatible drugs, and the protection of drugs from moisture, light and air.

For controlled release of drug suitable for parenteral administration, the size (diameter) of the microspheres should be large enough to provide adequate duration of release yet small enough to not restrict passage through the standard syringe needles employed. Thus, a desirable maximum size would be about 150 microns for a No. 20 gauge needle.

The processes of this invention can produce microspheres with diameters significantly less than 150 microns. For example, oil droplets of an emulsion may be reduced in size by brief ultrasonic homogenization prior to solvent removal to yield discrete microspheres of 5-25 microns, free of agglomerization. Submicron microspheres or a latex of submicron particles may be obtained by more extensive ultrasonic homogenization. The submicron particle size makes it amenable for intravenous application. These particles may also be used for oral or parenteral administration of poorly absorbing drugs due to the increased surface area available. Latex containing submicron particles of microencapsulated active material would also be suitable for topical application, including dermatological and cosmetic agents such as lotions, deodorants and fragrances.

The present emulsion process can also be used to prepare microspheres of polymer without drug or microspheres of drug without polymer. Immunologically active materials can be bound to microspheres of only polymers to serve as diagnostic agents for antigen-antibody reactions. These microspheres can also be bound to proteins and tagged with fluorescent dye or radioactive substance to label specific receptor site on cell membrane. Microspheres of drug without polymer may be used as core material for subsequent microencapsulation.

Microspheres preformed by the emulsion process of this invention including microcapsules, homogeneous microprills, or microspheres of only drug or polymer, may be used to prepare multiple encapsulated microcapsules, e.g., by the low temperature phase separation process described in U.S. Pat. No. 4,166,800. For example, multiple encapsulated microspheres may be prepared by preforming microspheres following the teaching of this invention and utilizing this dispersion of preformed microcapsules or homogeneous microprills in a polymer solution. In certain cases it may be necessary to lower the temperature ($-40°$ to $-100°$ C.) of the polymer solution prior to the introduction of the preformed microspheres to avoid dissolving the preformed microspheres in the polymer solution. This concept is especially useful for reducing the initial release rate, and therefore increases the duration of release, by depositing a layer of polymer as a barrier on preformed microspheres. This technique can be extended to create multilayered microspheres.

Multiple encapsulation can also be used to produce new microcapsules formed by controlled aggregation of one or more heterogeneous, preformed microspheres with or without one or more free drugs. For example, two or more drugs can be microencapsulated separately, either because of incompatability or lack of a common microencapsulation procedure suitable for all the component drugs. These preformed microcapsules can be combined and dispersed in a polymer solution for a subsequent microencapsulation to produce new microcapsules containing the previously encapsulated drug particles. Such compartmentalized microcapsules offer an advantage over a physical mixture in that uniformity is maintained by avoiding any uneven settling of the components upon storage.

Another application for compartmentalized microcapsules would be to segregate one or more reactants for subsequent reaction upon demand. Release for reaction can be effected by pressure, rupture, passage of time, exposure to water, air, light, heat or other triggering mechanism.

EXAMPLE 1

A solution of 1.0 g Parlodel ® (bromocriptine mesylate, Sandoz, Inc.) in 2 ml methanol was mixed with a solution of 1.0 g poly(D,L-lactic acid) in 10 ml methylene chloride. The organic solution was emulsified by swirling with an aqueous solution of 0.2 g sodium oleate, 15 ml 0.1 N NaOH and 85 ml distilled water. The organic solvents were removed by vacuum distillation at room temperature for 3 hours then at 30° C. for 2 hours. The product was vacuum filtered, washed with water, dried and weighed 1.74 g. Analysis indicated that the microencapsulated drug was converted from the mesylate salt to its free base form. Microscopic examination showed that the product was discrete microprills of about 25-90 micron diameter, free of agglomeration.

The release rate of bromocriptine mesylate from the microprills was determined by placing a sample containing the equivalent of 90 mg drug in a dissolution flask containing 1000 ml of pH 3.4 citrate buffer solution. The mixture was stirred at 500+ rpm at room temperature. Aliquots were withdrawn at various time points and assayed by measuring the absorbance at 300 nm with an ultraviolet spectrophotometer. The release rate of bromocriptine mesylate was:

|  | 1 hour | 4 hours | 1 day | 2 days | 3 days | 6 days |
| --- | --- | --- | --- | --- | --- | --- |
| % Released | 14 | 19 | 30 | 45 | 52 | 72 |

EXAMPLE 2

The procedure of Example 1 was followed except that the aqueous solution consisted of 1.64 g gelatin, 18 ml 0.1 N NaOH and 72 ml distilled water. The yield was 1.12 g of coarse agglomerates. The release rate of the drug in pH 3.4 buffer was:

|  | 1 hour | 4 hours | 1 day |
| --- | --- | --- | --- |
| % Released | 22 | 29 | 62 |

EXAMPLE 3

A solution of 1.0 g bromocriptine mesylate in 2 ml methanol was mixed with a solution of 1.0 g poly(D,L- lactic acid) in 20 ml methylene chloride. The organic solution was emulsified with an aqueous solution of 0.2 g potassium oleate, 15 ml 0.1 N KOH and 85 ml distilled water. The organic solvents were evaporated by stirring in an open beaker at room temperature for 4 hours. The product was filtered, washed with water and dried. The yield was 1.36 g of discrete microprills of 25–100 micron diameter.

EXAMPLE 4

A solution of 0.5 g bromocriptine mesylate in 3 ml methanol was mixed with a solution of 0.5 g poly(D,L-lactic acid) in 10 ml methylene chloride. The organic solution was emulsified with an aqueous solution of 0.1 g sodium oleate, 0.1 g Tween 20, 7.5 ml 0.1 N NaOH and 42.5 ml distilled water. The organic solvents were evaporated by stirring in an open beaker at room temperature. The product was filtered, washed with water and dried to yield discrete microprills with diameter of 20–100 microns.

EXAMPLE 5

The procedure of Example 4 was followed using only Tween 20 without sodium oleate. Massive agglomeration occurred and no microspheres were obtained.

EXAMPLE 6

The procedure of Example 1 was followed except that the aqueous solution consisted of 0.4 g acacia gum, 18 ml 0.1 N NaOH and 72 ml distilled water. While organic solvents were being removed by vacuum distillation at room temperature, massive agglomeration occurred and discrete microspheres were not obtained.

EXAMPLE 7

A solution of 0.5 g Hydergine ®[1] free base (Sandoz, Inc.) in 2 ml methanol was mixed with a solution of 0.5 g poly(D,L-lactic acid) in 10 ml methylene chloride. The organic solution was emulsified with an aqueous solution of 0.1 g sodium oleate, 7.5 ml 0.1 N NaOH and 42.5 ml distilled water. The organic solvents were evaporated by stirring in an open beaker at room temperature for 3 hours. The product was filtered, washed with water and dried. The yield was 0.85 g of discrete microprills of 25–125 micron diameter.
[1] An equimolar mixture of dihydroergocornine, dihydroergocristine and dihydroergokrptine.

EXAMPLE 8

A solution of 1.5 g Mellaril ® (thioridazine free base, Sandoz, Inc.) and 1.0 g poly(D,L-lactic acid) in 10 ml methylene chloride was emulsified with an aqueous solution of 0.2 g sodium oleate, 15 ml 0.1 N NaOH and 85 ml distilled water. The organic solvent was removed by vacuum distillation at 40° C. for 2 hours. The product was filtered, washed with water and dried to yield 2.05 g of discrete microprills with diameter of 10–50 microns.

EXAMPLE 9

A solution of 1.0 g temazepam and 1.0 g poly(D,L-lactic acid) in 10 ml methylene chloride was emulsified with an aqueous solution of 0.1 g sodium oleate in 60 ml distilled water. The organic solvent was removed by vacuum distillation at 40° C. for 0.5 hour. The product was filtered, washed with water and dried. The discrete microprills weighed 1.26 g and had a diameter of 25–150 microns.

EXAMPLE 10

A dispersion of 0.5 g Sudan Black B (partly soluble in methylene chloride) was sonicated for 3 minutes with a solution of 2.0 g poly(D,L-lactic acid) in 20 ml methylene chloride. The dispersion was emulsified with an aqueous solution of 0.6 g sodium oleate in 200 ml distilled water. The organic solvent was removed by vacuum distillation at room temperature for 2 hours then at 30° C. for 2 hours. The product was filtered, washed with water, dried and weighed 2.49 g. Microscopic examination showed discrete, dark blue microspheres of 20–85 micron diameter.

EXAMPLE 11

A solution of 0.4 g bromocriptine mesylate in 0.8 ml methanol was mixed with solution of 0.4 g polypropylene glycol fumarate (Dynatech Co., Cambridge, MA) in 4 ml methylene chloride. The organic solution was emulsified with an aqueous solution of 0.15 g sodium oleate, 6 ml 0.1 N NaOH and 49 ml distilled water. The organic solvents were removed by vacuum distillation at room temperature for 2 hours then at 30° C. for 2 hours. The product was filtered, washed with water, dried and weighed 0.61 g. Discrete microprills of 20–120 micron diameter were obtained.

EXAMPLE 12

A solution of 0.5 g poly(D,L-lactic acid) in 10 ml methylene chloride was emulsified with an aqueous solution of 0.15 g sodium oleate in 50 ml distilled water. The organic solvent was evaporated by stirring in an open beaker at room temperature for 1 hour. The product was filtered, washed with water, dried and weighed 0.38 g. The resulting discrete microprills of only polymer were 15–100 microns in diameter.

EXAMPLE 13

A solution of 0.5 g bromocriptine mesylate in 1 ml methanol was mixed with 10 ml methylene chloride. The organic solution was emulsified with an aqueous solution of 0.15 g sodium oleate, 7.5 ml 0.1 N NaOH and 42.5 ml distilled water. The organic solvents were evaporated by stirring in an open beaker at room temperature for 1.5 hours. The product was filtered, washed with water, dried and weighed 0.24 g. The resulting discrete microprills of only drug were 20–40 microns in diameter.

EXAMPLE 14

A solution of 0.5 g bromocriptine mesylate in 1 ml methanol was mixed with a solution of 0.5 g poly(D,L-lactic acid) in 10 ml methylene chloride. The organic solution was emulsified by swirling with an aqueous solution of 0.15 g sodium oleate, 7.5 ml 0.1 N NaOH and 42.5 ml distilled water. The 25–100 micron oil droplets of the resulting emulsion were further reduced to 5–25 microns by ultrasonic homogenization for 1 minute. The organic solvents were evaporated by stirring in an open beaker at room temperature. The product was filtered, washed with water and dried to yield 0.84 g of discrete microprills with a diameter of 5–25 microns.

EXAMPLE 15

A solution of 1.0 g bromocriptine mesylate in 2 ml methanol was mixed with a solution of 1.0 g poly(D,L-lactic acid) in 20 ml methylene chloride. The organic solution was emulsified with an aqueous solution of 0.2 g sodium oleate, 0.2 g gelatin, 15 ml 0.1 N NaOH and 85 ml distilled water. The organic solvents were removed by vacuum distillation at room temperature for 1 hour then at 30° C. for 2 hours. The product was filtered, washed with water and dried. The yield was 1.63 g of discrete microprills of 20–120 micron diameter, free of agglomeration.

I claim:

1. A process for the preparation of microspheres having a particulate core material encapsulated by a polymer coating which comprises, dissolving the polymer in a volatile, water-immiscible solvent in which the core material is not soluble, adding the core material particles, mixing the resulting dispersion with an aqueous solution containing sodium oleate or potassium oleate as an emulsifier to form an oil-in-water emulsion, and removing the solvent to form discrete microcapsules free of agglomerates.

2. The process according to claim 1 wherein the polymer is a biodegradable polymer.

3. The process according to claim 2 wherein the biodegradable polymer is polylactic acid, polyglycolic acid, polyhydroxybutyric acid, polycaprolactone, polyalkylene oxalate, or a polyalkylene glycol ester of acids of the citric acid cycle or copolymers thereof.

4. The process according to claim 3 wherein the polymer is polylactic acid.

5. The process according to claim 4 wherein the core material is selected from the group consisting of thioridazine, bromocriptine, a mixture of dihydroergocornine, dihydroergocristine, and dihydroergokryptine, and acid addition salts thereof.

6. The process according to claim 1 wherein the core material is a drug.

7. The process according to claim 6 wherein the polymer is a biodegradable polymer.

8. The process according to claim 1 wherein the polymer is selected from the group consisting of cellulosic polymers, polyvinylacetate, natural or synthetic rubbers, polyvinyl chloride, polyacrylates, and polystyrene.

9. A process for the preparation of microspheres having homogeneous mixture of a polymer and core material which comprises, dissolving the polymer and core material in a volatile, water-immiscible solvent, mixing the polymer-core material-solvent system with an aqueous solution containing sodium oleate or potassium oleate as an emulsifier to form an oil-in-water emulsion, and removing the solvent to form discrete microprills free of agglomerates.

10. The process, according to claim 9 wherein the polymer is a biodegradable polymer.

11. The process according to claim 10 wherein the biodegradable polymer is polylactic acid, polyglycolic acid, polyhydroxybutyric acid, polycaprolactone, polyalkylene oxalate, or a polyalkylene glycol ester of acids of the citric acid cycle or copolymers thereof.

12. The process according to claim 11 wherein the polymer is polylactic acid.

13. The process according to claim 12 wherein the core material is selected from the group consisting of thioridazine, bromocriptine, a mixture of dihydroergocornine, dihydroergocristine, and dihydroergokryptine, and acid addition salts thereof.

14. The process according to claim 9 wherein the core material is a drug.

15. The process according to claim 14 wherein the polymer is a biodegradable polymer.

16. The process according to claim 9 wherein the polymer is selected from the group consisting of cellulosic polymers, polyvinylacetate, natural or synthetic rubbers, polyvinyl chloride, polyacrylates, and polystyrene.

* * * * *